(12) United States Patent
Foo et al.

(10) Patent No.: US 6,192,264 B1
(45) Date of Patent: Feb. 20, 2001

(54) METHOD AND SYSTEM FOR MRI VENOGRAPHY INCLUDING ARTERIAL AND VENOUS DISCRIMINATION

(75) Inventors: Thomas K. F. Foo, Rockville; Vincent B. Ho, North Bethesda, both of MD (US); Steven D. Wolff, New York, NY (US)

(73) Assignees: General Electric Company, Milwaukee, WI (US); Uniformed Services University of Health Sciences, Bethesda, MD (US)

( * ) Notice: Under 35 U.S.C. 154(b), the term of this patent shall be extended for 0 days.

(21) Appl. No.: 09/221,500

(22) Filed: Dec. 28, 1998

(51) Int. Cl.$^7$ ................................................. A61B 5/055
(52) U.S. Cl. ........................................ 600/413; 324/309
(58) Field of Search ................................. 600/410, 411, 600/413, 419; 324/307, 309

(56) References Cited

U.S. PATENT DOCUMENTS

| | | | |
|---|---|---|---|
| 4,602,641 | * | 7/1986 | Feinberg ............................. 600/410 |
| 4,609,872 | * | 9/1986 | O'Donnell ........................... 324/306 |
| 4,752,734 | * | 6/1988 | Wedeen ............................... 324/306 |
| 4,947,120 | * | 8/1990 | Frank ................................... 324/309 |
| 4,995,878 | | 2/1991 | Rai ....................................... 606/194 |
| 5,315,997 | | 5/1994 | Widder et al. ..................... 128/653.3 |
| 5,408,180 | * | 4/1995 | Mistretta et al. ................... 324/306 |
| 5,445,812 | | 8/1995 | Gotou .................................. 424/9.4 |
| 5,521,502 | * | 5/1996 | Siegel, Jr. et al. ................. 324/306 |
| 5,799,649 | * | 9/1998 | Prince .................................. 600/420 |
| 5,830,143 | * | 11/1998 | Mistretta et al. ................... 600/420 |
| 5,929,637 | * | 7/1999 | Taguchi et al. ..................... 324/306 |
| 6,073,042 | * | 6/2000 | Simonetti ............................ 600/420 |

OTHER PUBLICATIONS

Wedeen, VJ, et al., *Projective Imaging of Pulsatile Flow with Magnetic Resonance*, Science, 1985; vol. 230, pp. 946–948.

Lebowitz, JA, et al. *Gadolinium–Enhanced Body MR Venography with Subtraction Technique*, AJR:169, Sep. 1997, pp. 755–758.

Steffens, JC, et al., *Cardiac–Gated Two–Dimensional Phase Contrast MR Angiography of Lower Extremity Occlusive Disease*, AJR:169, Sep. 1997, pp. 749–754.

Pelc, Norbert J., et al., *Quantitative Magnetic Resonance Flow Imaging*, Magnetic Resonance Quarterly, vol. 10, No. 3, pp. 125–147.

Nishimura, Dwight, et al., *Magnetic Resonance Angiography*, IEEE Transactions on Medical Imaging, vol. MI–5, No. 3, Sep. 1986.

(List continued on next page.)

*Primary Examiner*—Brian L. Casler
(74) *Attorney, Agent, or Firm*—Boyle, Fredrickson; Christian G. Cabou; Phyllis Y. Price (57) ABSTRACT

A system and method for arterial and venous discrimination in MR venography is disclosed. By setting a noise level in the phase image (that is proportional to the velocity encoding value) at a threshold level between that of the arterial signals and the venous signals during the diastole portion of the cardiac cycle and acquiring a phase contrast MR image during the diastole portion, the arterial signals are effectively suppressed and a venous only image can be reconstructed. Post-processing steps are disclosed which can alternatively provide an arterial only image. By separately reconstructing a magnitude image and a phase image map to produce a magnitude image and a phase image, a masking module can create an output displaying venous only or arterial only images based on a user selection. The present invention allows for a complete noninvasive angiography exam to be completed within approximately 30 minutes.

24 Claims, 4 Drawing Sheets

OTHER PUBLICATIONS

Walker, M.F., et al., *Quantitative Flow Measurement in Phase Contrast MR Angiography,* Journal of Computer Assisted Tomography, 12(2), pp. 304–313, Mar./Apr. 1988.

Moran, Ph.D., Paul R., *A Flow Velocity Zeugmatographic Interlace for NMR Imaging in Humans,* Magnetic Resonance Imaging, vol. 1, pp. 197–203, 1982.

Moran, Ph.D., Paul R., et al., *Verification and Evaluation of Internal Flow and Motion,* Radiology 1985; 154: 433–441.

Firmin, D.N., et al., *In Vivo Validation of MR Velocity Imaging,* Journal of Computer Assisted Tomography, vol. 11, No. 5, 1987, pp. 751–756.

Bernstein, Ph.D., Matt A., et al., *Comparison of Phase-Difference and Complex-Difference Processing in Phase-Contrast MR Angiography,* JMRI Nov./Dec. 1991, vol. 1, No. 6, pp. 725–729.

Bernstein, Ph.D., Matt A., et al., *Minimizing TE in Moment-nulled or Flow-encoded Two- and Three-dimensional Gradient-Echo Imaging,* JMRI, Sep. 1992, vol. 2, No. 5, pp. 583–588.

* cited by examiner

METHOD AND SYSTEM FOR MRI VENOGRAPHY INCLUDING ARTERIAL AND VENOUS DISCRIMINATION

BACKGROUND OF THE INVENTION

The present invention relates generally to magnetic resonance imaging (MRI) and more particularly, to a system and method to discriminate between venous and arterial blood flow and for MRI venography.

MRI utilizes radio frequency pulses and magnetic field gradients applied to a subject in a strong field to produce viewable images. Contrast agents are used to improve MR images. Such contrast agents include magnetizable substances having metals or metallic compounds. Such contrast agents may be paramagnetic, ferromagnetic, or superparamagnetic and acts through dipole interactions with tissue protons. Most MR imaging contrast agents have similar mechanisms of action. Most are based on gadolinium chelates and therefore, are paramagnetic agents that develop a magnetic moment when placed in a magnetic field.

With the increasing use of MR contrast agents for MR angiography (MRA), arterial and venous signals become equally enhanced. The reduced $T_1$ relaxation time removes the possibility of using spatial saturation RF pulses to eliminate either arterial or venous signals for flow discrimination. Automatic bolus detection merely addresses this issue by triggering the acquisition only when the flow is in the arterial phase. However, with the contrast already on board, subsequent acquisitions must contend with the increased venous signal intensity as the contrast agent continues to distribute in the system. In addition, the expected use of intravascular contrast agents with much longer persistence will require more novel techniques for arterial-venous discrimination.

Phase contrast magnetic resonance angiography (MRA) is a practical and clinically applicable technique for imaging blood flow. MRA makes use of flow encoding gradient pulses which impart a velocity-dependent phase shift to the transverse magnetization of moving spins while leaving stationary spins unaffected. Each phase contrast acquisition generates two images; a magnitude image that is proportional to the proton density of the object and may also be $T_1$-weighted, and an image representing the phase of the object. The phase image produced has information only from the moving spins and the surrounding stationary tissue is suppressed. Images representing both the average flow over the entire cardiac cycle and at a series of individual points in the cycle have been generated using this technique. The phase contrast MR method produces phase images with intensities that represent the magnitude of the flow velocity and also the direction of flow. Therefore, such images may be used for both qualitative observation of blood flow and quantitative measurement. The practical application of phase contrast MR angiography and venography to the quantitative determination of flow velocity is therefore evident.

In a phase contrast image, the phase shifts generated in a pixel by moving spins is directly proportional to the motion of the ensemble of spins. If the velocity is linear, then the phase shift is directly proportional to the velocity and the sign of the phase shift is indicative of the direction of flow. As phase representation are in terms of an angle, unique values of flow velocity and direction of motion can be obtained if the phase shifts are constrained between ±π. That is, the velocity encoding value or VENC, is given by:

$$VENC = \frac{\pi}{\gamma \Delta M_1},$$

where $\gamma$ is the gyromagnetic ratio, and $\Delta M_1$ is the gradient moment and is proportional to the area of the flow encoding gradient waveform. This value of VENC is such that all flow velocities will have values constrained between ±π. The noise level in the phase image is also proportional to the velocity encoding value. It can be shown that the noise level in the phase image, $\sigma_v$, is related to the VENC value by:

$$\sigma_v^2 = \frac{2VENC^2 \sigma^2}{\pi^2 |M|^2},$$

where M is the magnitude of the spins in a voxel, and σ is the noise variance of the acquisition. Thus, by raising the VENC value, the noise level in the phase image increases correspondingly.

Quantitative flow data can readily aid in the diagnosis and management of patients and also help in the basic understanding of disease processes. There are many techniques available for the measurement of blood flow, including imaging based methods using radiographic imaging of contrast agents, both in projection and computed tomography (CT), ultrasound, and nuclear medicine techniques. Radiographic and nuclear medicine techniques require the use of ionizing radiation and/or contrast agents. Some methods involve making assumptions about the flow characteristics which may not necessarily be true in vivo or require knowledge about the cross-sectional area of the vessel or the flow direction. Ultrasound techniques are difficult to apply in certain situations because of intervening bone or air.

In one prior art time-of-flight MRA technique that gates the acquisition to systole and diastole to generate an image with enhanced arterial flow in systole, a second image is provided with less arterial flow enhancement in diastole. The venous flow in both images would be approximately the same, however. See Pulmonary Vasculature: Single Breath-Hold MR Imaging With Phased Array Coils. *Radiology* 1992; 183: 473–477, Foo TKF, Maclall J R, Hayes C E, Sostman H D, and Slayman B E. By subtracting the two images, the common venous flow mode can be eliminated, together with the stationary background noise. However, such a technique is not practical and patients with peripheral artery disease where the difference in flow between the systole and diastole is not significant. Other techniques which attempted to distinguish between arterial and venous flow require imaging during a first pass of the contrast agent, and then subtracting the images from the initial arterial phase from a latter venous or equilibrium pass. Such techniques have been found to be too dependent upon the unpredictable flow of the contrast agent in the patient.

It would therefore be desirable to have a method and apparatus for venography that efficiently discriminates between arterial and venous signals to create a venous only image or an arterial only image using magnetic resonance imaging.

SUMMARY OF THE INVENTION

The present invention relates to a system and method for magnetic resonance (MR) venography that can efficiently discriminate between arterial and venous signals to display either an arterial image, without venous representation, or a venous image, without an arterial representation, that solves the aforementioned problems.

The present invention is preferably implemented using an MR phase contrast image acquisition designed to efficiently discriminate between arteries and veins using a segmented k-space fast-phase contrast pulse sequence to acquire images that are sensitive only to venous flow. This technique is accomplished by gating the acquisition to the diastolic portion of the cardiac cycle where arterial flow is minimal. By selecting a sufficiently high velocity encoding value during diastole, the arterial flow signal is suppressed in a phase image, but is present in the accompanying magnitude image. By using the phase image as a template, the venous signal can either be subtracted from the magnitude image, thereby producing an MR arteriogram, or the magnitude image and the phase image can be masked to produce an MR venogram.

Such a pulse sequence acquisition can acquire a flow directional sensitive image quite rapidly. If the acquisition is gated to diastole, where arterial flow is minimal, the phase image will have a non-zero intensity for the venous component only. The magnitude image on the other hand, will contain both arterial and venous signals, assuming that the flow is predominately in the superior-inferior direction, as in the peripheral vasculature. Therefore, only one flow encoding gradient direction is necessary.

Therefore, in accordance with one aspect of the invention, a method of discriminating between arteries and veins in MR venography includes the steps of setting a velocity encoding value at a threshold level above that of undesirable arterial flow velocity signals during a diastolic portion of the cardiac cycle and acquiring a phase contrast MR image during that diastolic portion. The undesirable arterial flow velocity signals are then suppressed during this data acquisition. An MR image is then reconstructed displaying only the desirable flow velocity signals without the undesirable flow velocity signals. In other words, the system can efficiently display an arterial only image or a venous only image.

In accordance with another aspect of the invention, an MRI apparatus for MR venography is disclosed that is capable of discriminating veins from arteries which includes an MRI system having a number of gradient coils positioned about a bore of a magnet to impress a polarizing magnetic field and an RF transceiver system and an RF modulator controlled by a pulse control module to transmit RF signals to an RF coil assembly to acquire MR images. The MRI apparatus also includes a computer programmed to activate the MRI system in a prescan mode to acquire an arterial signal from a patient and monitor a magnitude of the arterial signal during a diastolic portion of the cardiac cycle. The computer is also programmed to set a velocity encoding value at a level higher than the monitored magnitude of the arterial signal and activate the MRI system to acquire a phase contrast image during diastole using the velocity encoding value as a noise threshold. Such a system can then provide a phase map image and a magnitude image, wherein the phase map image has arterial signals suppressed, providing a well defined venous signal phase image map. The magnitude image will still have the arterial and venous signals therein. A masking routine can provide the venous only image or the arterial only image.

Suppression of arterial signal is achieved by exploiting a feature of phase contrast MR angiography. In phase contrast MR angiography, the velocity encoding or VENC value determines the noise floor in the phase image. This noise floor is directly proportional to the VENC value and is given in units of velocity. Spins with velocity below that of the noise floor are not evident in the phase image.

Hence, by increasing the VENC value, signals from slower moving spins in the phase image are suppressed. As the arterial velocity in diastole is smaller than that of the venous velocity, signals from arterial structures are suppressed in diastolicgated phase contrast acquisitions.

In accordance with yet another aspect of the invention, a venography system to discriminate venous blood flow from arterial blood flow and display an MR image with only a representation of either the arterial blood flow or the venous blood flow includes an MRI apparatus capable of producing arterial and venous signals from a monitored patient, and a user interface is provided to select an MR image from a group consisting of an arterial only blood flow image and a venous only blood flow image. The system includes a velocity encoding module connected to the MRI apparatus to receive the arterial and venous signals from the MRI apparatus and produce a velocity encoding value having a magnitude between that of the arterial signal and that of the venous signal during a cardiac diastolic period of an MR image. An image reconstruction module is connected to the velocity encoding module to produce a magnitude image and a phase image. A mask module is connected to receive the magnitude and phase images and produce either one of the venous only blood flow image or the arterial only blood flow image based on an input to the user interface.

In accordance with yet another aspect of the invention, an MR venography apparatus for displaying only one of venous blood flow and arterial blood flow includes a means for acquiring an MRI, a means for ECG-gating MRI acquisitions during a diastolic period of the cardiac cycle. and a means for encoding a velocity encoding value for suppressing arterial blood flow signals during the diastolic period MRI acquisitions. The MR venography apparatus also includes a means for reconstructing a magnitude image and a phase map image and a means for processing the reconstructed magnitude and phase map images to create venous only and arterial only output signals. A means for displaying one of the venous only output signals as a venous blood flow image and the arterial only output signal as an arterial blood flow image is also provided.

Various other features, objects and advantages of the present invention will be made apparent from the following detailed description and the drawings.

BRIEF DESCRIPTION OF THE DRAWINGS

The drawings illustrate the best mode presently contemplated for carrying out the invention.

In the drawings.

DETAILED DESCRIPTION OF THE PREFERRED EMBODIMENT

Figure 1:
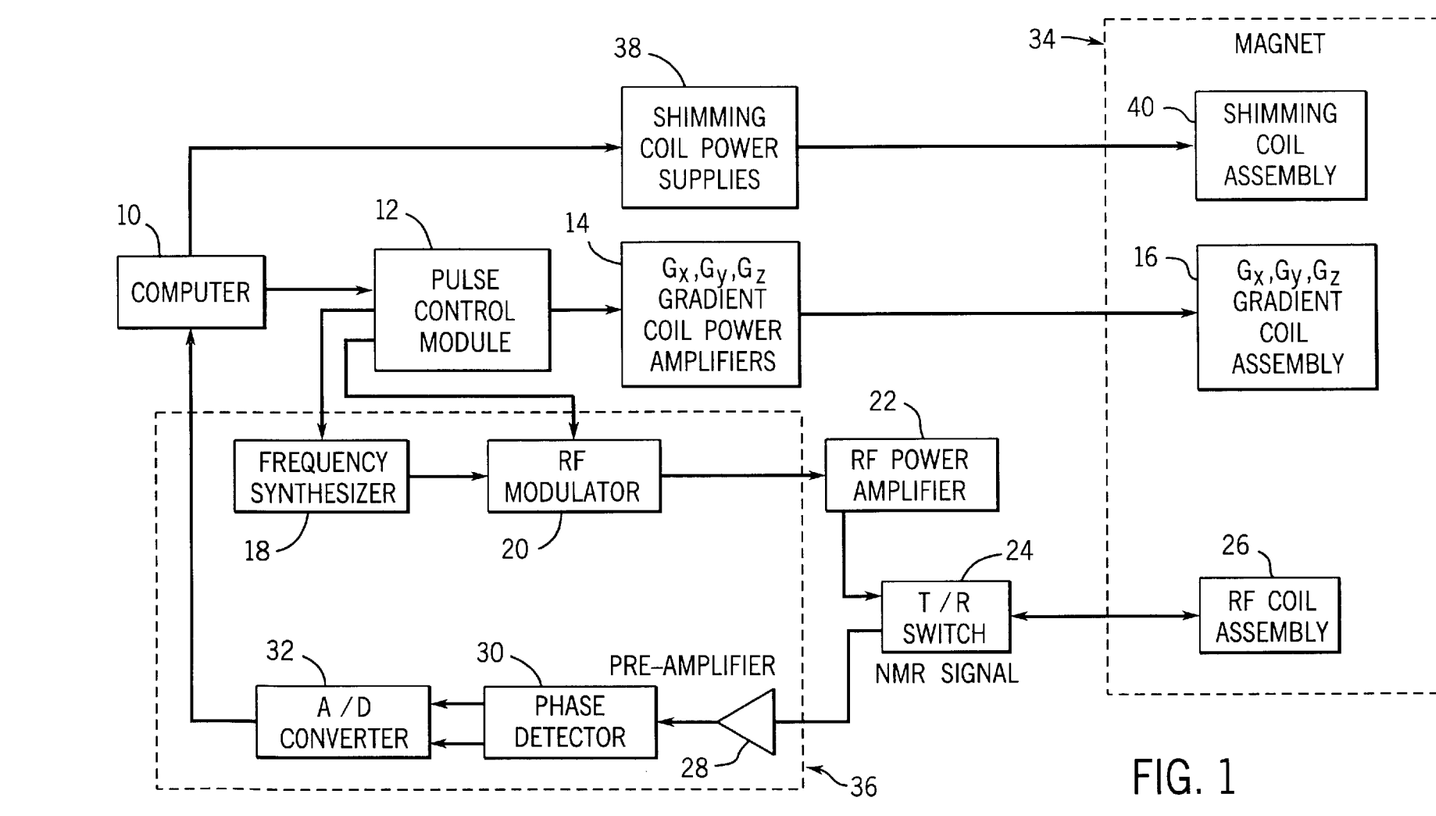
FIG. 1 is a schematic block diagram of an MR imaging system for use with the present invention.

Referring to FIG. 1, a magnetic resonance (MR) imaging system of a type suitable for the practice of the invention includes a computer 10 which controls gradient coil power amplifiers 14 through a pulse control module 12. The pulse control module 12 and the gradient amplifiers 14 together produce the proper gradient waveforms Gx, Gy, and Gz, for either a spin echo, a gradient recalled echo pulse sequence, a fast spin echo, or other type of pulse sequences. The gradient waveforms are connected to gradient coils 16 which are positioned around the bore of the magnet 34 so that gradients Gx, Gy, and Gz are impressed along their respective axes on the polarizing magnetic field Bo from magnet 34.

The pulse control module 12 also controls a radio frequency synthesizer 18 which is part of an RF transceiver system, portions of which are enclosed by dashed line block 36. The pulse control module 12 also controls an RF modulator 20 which modulates the output of the radio frequency synthesizer 18. The resultant RF signals, amplified by power amplifier 22 and applied to RF coil 26 through transmit/receive switch 24, are used to excite the nuclear spins of the imaged object (not shown).

The MR signals from the excited nuclei of the imaged object are picked up by the RF coil 26 and presented to preamplifier 28 through transmit/receive switch 24, to be amplified and then processed by a quadrature phase detector 30. The detected signals are digitized by a high speed A/D converter 32 and applied to computer 10 for processing to produce MR images of the object. Computer 10 also controls shimming coil power supplies 38 to power shimming coil assembly 40.

The present invention includes a method and system for MRI venography that includes arterial and venous discrimination for use with the above-referenced MRI system, or any similar or equivalent system for obtaining MR images.

Figure 2:
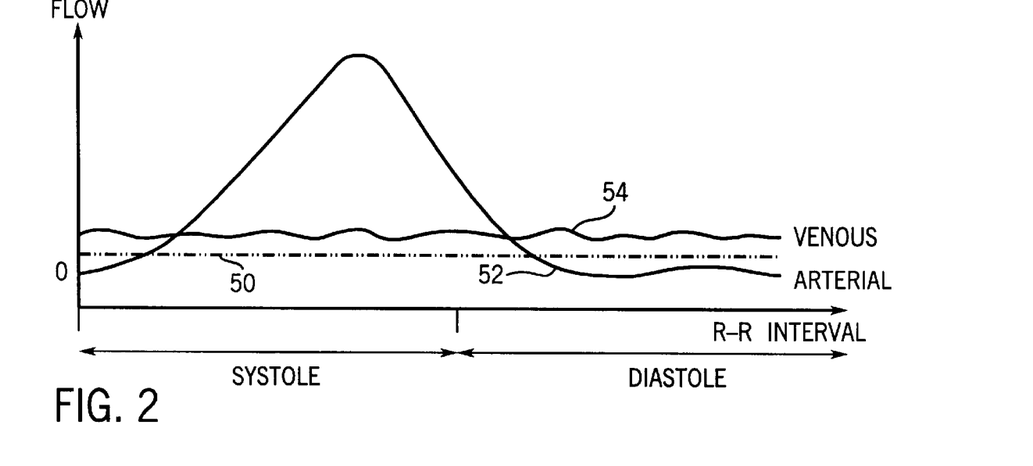
FIG. 2 is a graphical representation of arterial and venous flow velocities during a cardiac cycle.

Referring to FIG. 2, a typical cardiac R-R interval is shown in which the venous and arterial flow velocities are depicted in the descending aorta during systole and diastole. As shown, the dominant arterial flow is in systole. This tri-phasic flow velocity profile for arterial blood is typical of the peripheral vasculature. The present invention includes a method of discriminating between arteries and veins in MR venography. In order to do so, a velocity encoding (VENC) value 50 is set at a threshold level such that the noise level in the phase image is above that of the arterial signal 52 during the diastolic portion of the cardiac cycle, but below that of the venous signal 54, also in the phase image.

Figure 3:
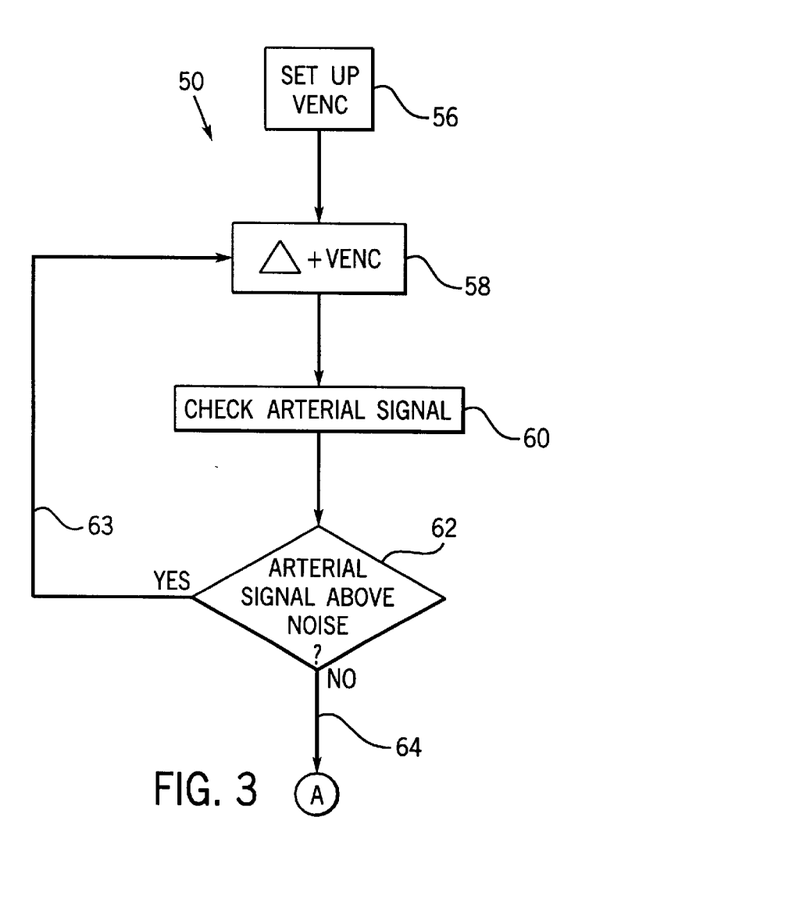
FIG. 3 is a flow chart of a portion of the system and method of the present invention.

Referring to FIG. 3, in order to set the VENC value 50, a setup VENC value subroutine 56 first increments the previous VENC value 58 and monitors the arterial signal during the diastolic period of the cardiac cycle 60. A comparison is then made between the arterial signal and the VENC value 62, and if the arterial signal is above the noise level for the VENC value 63, then the VENC value is incremented at 58 and the steps of monitoring the arterial phase signal 60 and comparing the arterial phase signal to the noise level corresponding to the VENC value 62 are repeated. Otherwise, when the noise corresponding to the VENC value, is above the arterial phase signal 64, the present setting of the velocity encoding value is provided for use in acquiring a phase contrast image.

Figure 4:
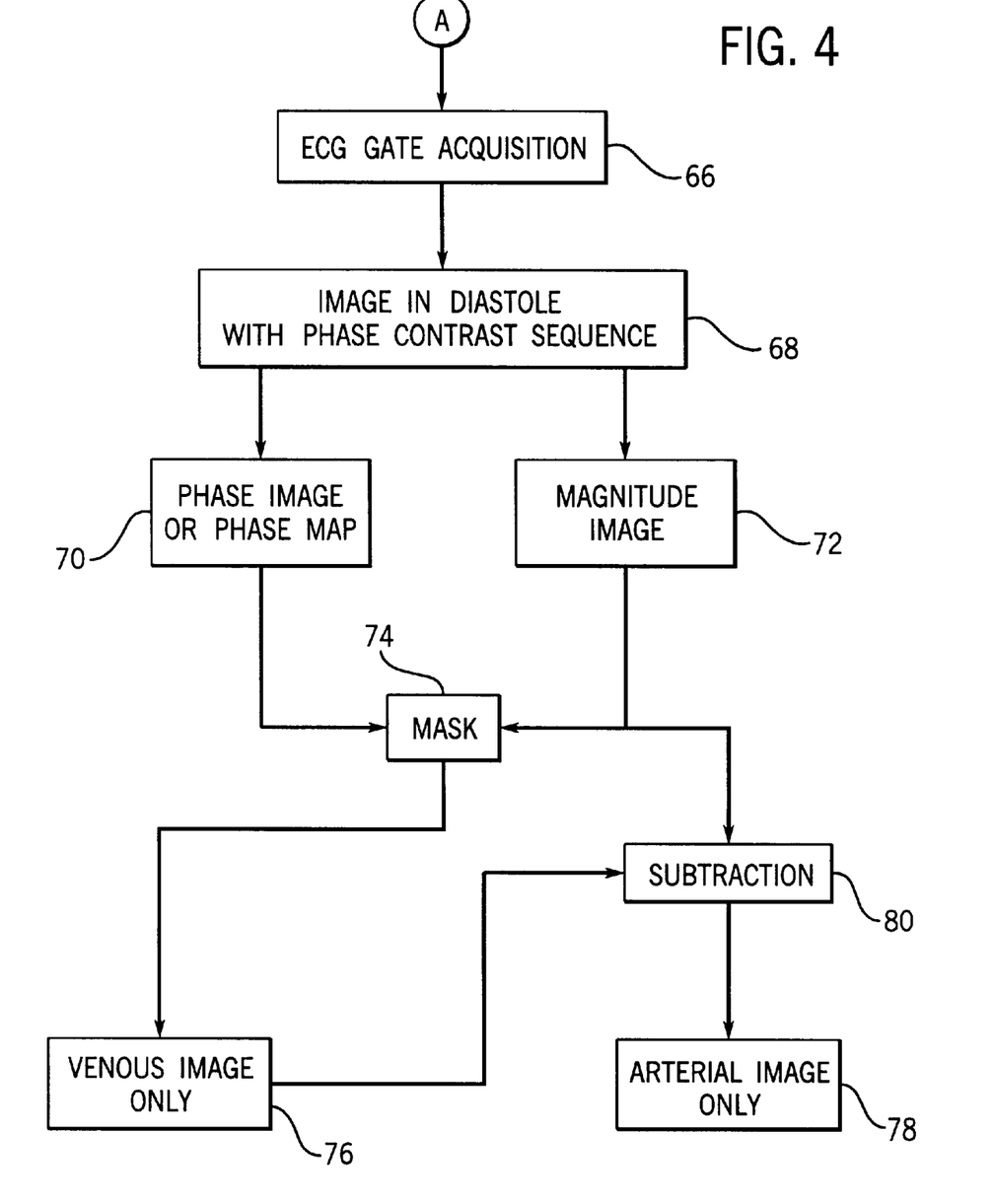
FIG. 4 is a flow chart of a portion of the system and method of the present invention.

Referring to FIG. 4, once the VENC value has been set, an electrocardiograph (ECG) gated MRI acquisition is initiated at 66. The method includes acquiring the phase contrast MR image during the diastolic period of the cardiac cycle 68 where the undesirable arterial flow velocity phase signals are below that of the noise level in the phase image corresponding velocity encoding value such that the undesirable flow velocity phase signals may be suppressed and the desirable venous flow velocity phase signals are acquired. Hence, the phase image would be preferential to venous flow velocities above the noise level. As a result, a phase image map 70 and a magnitude image 72 are reconstructed. By masking 74 the phase map image 70 with the magnitude image 72, a venous only image 76 can be acquired. If an arterial only image is desired 78, then the venous only image 76 is subtracted 80 from the magnitude image 72. As is now evident, the step of flow encoding the acquired phase contrast MR image is preferably done in a single flow direction.

In one embodiment, the masking step 74 is further defined as multiplying the phase map image and the magnitude image to acquire an MR data set capable of reconstruction as a venous only image 76. In doing so, by setting the pixel values in the phase image to unity whenever the phase value is above the noise level or floor, and thus generating a mask, and multiplying the phase-generated mask with the magnitude image, a venous only magnitude image is attainable. On the other hand, by setting the pixel values in the phase-generated mask image to zero and multiplying the phase-generated mask image with the magnitude image, an arterial only magnitude image can be acquired. In this embodiment, the subtraction step 80 is then not required.

Accordingly, an MRI apparatus for use with MR venography is disclosed that is capable of discriminating blood flow in veins from blood flow in arteries. Such an MRI apparatus for MR venography includes a magnetic resonance imaging system, such as that disclosed with reference to FIG. 1, and a computer 10, programmed to activate the MRI system in a prescan mode to acquire an arterial signal from a patient during the diastolic portion of a cardiac cycle and monitoring the magnitude of the arterial signal to set a velocity encoding value at a level such that the noise level in the phase image is higher than the monitored phase value of the arterial signal. The computer 10 is further programmed to activate the MRI system to acquire a phase contrast image 68, FIG. 4, during diastole using the velocity encoding value, as acquired from FIG. 3, to establish a corresponding noise threshold in the phase image to suppress the arterial signal. In accordance with this aspect of the invention, the computer is programmed to set the velocity encoding value by comparing the acquired arterial signal in the phase image to the noise level in the same phase image corresponding to the velocity encoding value, and if the noise level set by the velocity encoding value is greater than the acquired arterial signal in the phase image, then the velocity encoding value is incremented. Otherwise, the velocity encoding value is used during activation of the MRI system. The computer 10 is further programmed to acquire a phase map image 70 and a magnitude image 72, wherein the phase map image 70 has arterial signal suppressed, thereby providing a well defined venous signal phase image map. The magnitude image 70 would still contain the arterial and venous signals as a magnitude. The computer 10 is further programmed to mask the phase image map and the magnitude image map to acquire an image displaying either a venous only image or an arterial only image.

The MR image acquired is preferably, a segmented phase contrast pulse sequence MR image acquired substantially within the diastolic portion of the cardiac cycle while blood flows in a single direction. In one embodiment, the computer is programmed to display a venous only image with a magnitude by setting a pixel phase value to unity and multiplying the pixel phase value by the magnitude image. In this embodiment, in order to display the arterial only image, the pixel phase value is set to zero and the pixel phase value is multiplied by the magnitude image, thereby providing an arterial only image.

Figure 5:
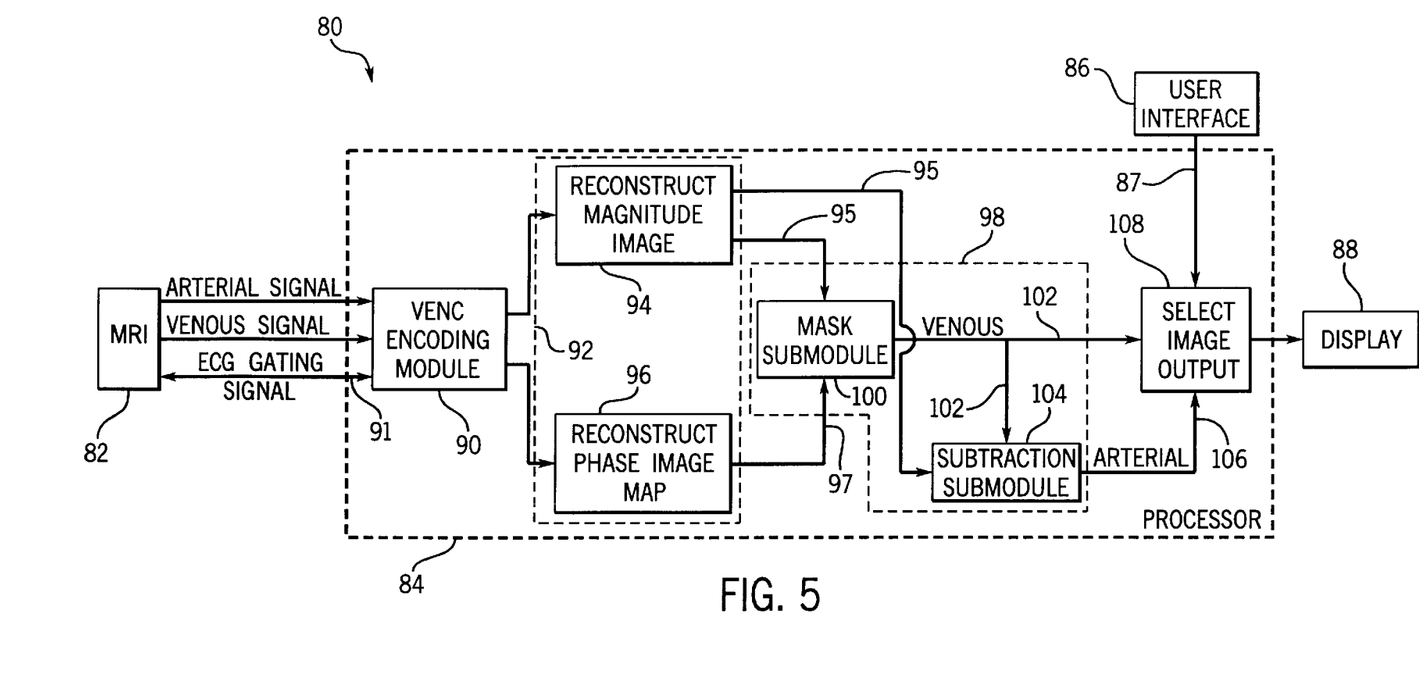
FIG. 5 is a schematic block diagram of the present invention.

Referring now to FIG. 5, a venography system 80 is disclosed to discriminate venous blood flow from arterial blood flow and display an MR image with a representation of either the arterial blood flow without venous flow or the venous blood flow without arterial flow. The venography system 80 includes an MRI apparatus 82 similar to that disclosed with reference to FIG. 1 and capable of producing arterial and venous signals from a monitored patient and activated by an ECG-gating signal from a processor 84. The venography system 80 also has a user interface 86 and a display monitor 88. The processor 84 includes a velocity encoding (VENC) module 90 in electrical communication with the MRI apparatus 82 to receive the arterial and venous signals. The VENC module 90 produces the velocity encoding value that sets the noise level in the phase image between that of the arterial phase signal value and that of the venous phase signal value as monitored during a prescan of the cardiac diastolic period of an MR image. Processor 84 also includes an image reconstruction module 92 having a magnitude image reconstruction submodule 94 and a phase image reconstruction submodule 96. The magnitude image reconstruction submodule 94, in the image reconstruction module 92 is connected to the velocity encoding module to produce a magnitude image 95. The phase image reconstruction submodule 96, in the image reconstruction module 92, is connected to the velocity encoding module 90 to produce the phase image 97. A mask module 98 is connected to receive the magnitude and phase images 95, 97 and produce either a venous only blood flow image 102 or an arterial only blood flow image 106 based on an input 87 to the processor 84 from the user interface 86. The mask module 98 includes a mask submodule 100 to multiply the phase map image 97 and the magnitude image 95 to create an MR data set capable of reconstruction as a venous only image 102. By subtracting the venous only image 102, in a subtraction submodule 104, from the magnitude image 95, an arterial only image 106 is created that is capable of display as an arterial only blood flow image. The venography system 80 also includes within processor 84, an image selection module 108 connected to the mask module 98 and the user interface 86 to select a desired image and provide a desired output to display 88. The image selection module 108 receives the venous only signals 102 and the arterial only signals 106 to display either a venous only image or an arterial only image, as selected by the user interface 86.

In another embodiment, which can be equivalently described with reference to FIG. 5, an MR venography apparatus for displaying either a venous blood flow or an arterial blood flow includes a means for acquiring an MR image 82, and a means for ECG-gating MRI acquisitions 90 during a diastolic period of a cardiac cycle with an ECG-gating signal 91. This MR venography apparatus also includes a means 90 for encoding a velocity encoding value for suppressing arterial blood flow signals during the diastolic period MRI acquisitions. The apparatus includes a means for reconstructing 92 a magnitude image 95 and a phase map image 97 and a means for processing 98 the reconstructed magnitude 95 and the phase map 97 images to create a venous only output signal 102 and an arterial output signal 106. A means for displaying 88 either a venous blood flow image or an arterial blood flow image is included and connected to an output means 108 for selecting which of the venous blood flow and arterial blood flow images to display. Preferably, the selection control output means 108, for directing which of the venous and arterial blood flow images is displayed on the means for displaying 88, is connected to a user interface means 86.

The means for processing 98 includes a means for masking 100 the magnitude image 95 with the phase map image 97 to create a venous only image 102. The means for reconstructing 98 also includes a means for subtracting 104, to subtract the result from the means for masking 100 from the magnitude image 95. It is understood that the foregoing description is just one example of the claimed MR venography apparatus and is merely one example for determining equivalents.

The present invention preferably utilizes a segmented k-space, ECG-gated phase contrast pulse sequence acquisition of between 32–64 views per segment to reduce MRI acquisition time. However, any fast ECG-gated phase contrast acquisition will suffice. It has been found that with this ECG-gated acquisition and the flow encoding being in a single direction, between 20–27 slice coronal or oblique coronal locations can be acquired in less than 4 min. This thus allows the possibility of completing a fast MR peripheral venography or angiography examination within 30 minutes.

The present invention has been described in terms of the preferred embodiment, and it is recognized that equivalents, alternatives, and modifications, aside from those expressly stated, are possible and within the scope of the appending claims.

What is claimed is:

1. A method of discriminating between arteries and veins in MR venography comprising the steps of:
    setting a velocity encoding value to establish a noise level above that of undesirable flow velocity signals during a portion of a cardiac cycle;
    acquiring a phase contrast MR image during the portion of the cardiac cycle where undesirable flow velocity signals is below that of the noise level established by the velocity encoding value thereby suppressing the undesirable flow velocity signals and acquiring desirable flow velocity signals; and
    reconstructing an MR image displaying desirable flow velocity signals without the undesirable flow velocity signals.

2. The method of claim 1 wherein the step of acquiring a phase contrast MR image further comprises the steps of:
    acquiring a phase map image and a magnitude image, the phase map image having arterial signals suppressed, thereby providing a well defined venous signal phase image map, and the magnitude image having both arterial and venous signals therein; and
    masking the phase map image and the magnitude image to acquire an image displaying one of a venous only image and an arterial only image.

3. The method of claim 2 wherein the step of acquiring a phase contrast MR image is further defined as acquiring the MR image substantially during diastole and the masking step is further defined as multiplying the phase map image and the magnitude image to acquire an MR data set capable of reconstruction as a venous only image.

4. The method of claim 2 wherein the masking step further comprises the steps of:
    setting a phase magnitude value to one and multiplying the phase value by the magnitude image to acquire the venous only image with a magnitude; and
    setting the phase magnitude value to zero and multiplying the phase value by the magnitude image to acquire the arterial only image with a magnitude.

5. The method of claim 1 wherein the MR image acquired is a segmented phase contrast pulse sequence MR image acquired substantially within a diastole portion of the cardiac cycle.

6. The method of claim 1 further comprising the step of flow encoding the acquired phase contrast MR image in a single flow direction.

7. The method of claim 1 wherein the undesirable flow velocity signals acquired in the step of acquiring a phase contrast MR image are arterial flow velocity signals.

8. The method of claim 1 wherein the step of setting a velocity encoding value is further defined as:

monitoring an arterial signal during a diastolic period of the cardiac cycle;

comparing the arterial signal to the noise level set by the velocity encoding value; and if the arterial signal is greater than the noise level in the phase image corresponding to the velocity encoding value, then incrementing the velocity encoding value and repeating the comparing step, otherwise, providing the velocity encoding value for use in the MR image acquisition step.

9. An MRI apparatus for MR venography capable of discriminating veins from arteries comprising:

a magnetic resonance imaging (MRI) system having a plurality of gradient coils positioned about a bore of a magnet to impress a polarizing magnetic field and an RF transceiver system and an RF modulator controlled by a pulse control module to transmit RF signals to an RF coil assembly to acquire MR images; and a computer programmed to:

activate the MRI system in a prescan mode to acquire an arterial signal from a patient;

monitor a magnitude of the arterial signal during a diastolic portion of a cardiac cycle;

set a velocity encoding value at a level higher than the monitored magnitude of the arterial signal; and activate the MRI system to acquire a phase contrast image during diastole using the velocity encoding value as a noise threshold.

10. The MRI apparatus of claim 9 wherein the computer is further programmed to:

compare the acquired arterial signal to a velocity encoding value and if the velocity encoding value is not greater than the acquired arterial signal, then incrementing the velocity encoding value; otherwise, use the velocity encoding value during activation of the MRI system.

11. The MRI apparatus of claim 9 wherein the computer is further programmed to:

acquire a phase map image and a magnitude image, the phase map image having arterial signals suppressed, thereby providing a well defined venous signal phase image map, and the magnitude image having both arterial and venous signals therein; and mask the phase image map and the magnitude image to acquire an image displaying one of a venous only image and an arterial only image.

12. The MRI apparatus of claim 11 wherein the computer is further programmed to:

set a phase magnitude value to one and multiply the phase value by the magnitude image to acquire the venous only image with a magnitude; and set the phase magnitude value to zero and multiply the phase value by the magnitude image to acquire the arterial only image with a magnitude.

13. The MRI apparatus of claim 9 wherein the MR image acquired is a segmented phase contrast pulse sequence MR image acquired substantially within a diastole portion of the cardiac cycle.

14. The MRI apparatus of claim 9 wherein the computer is further programmed to acquire the phase contrast image which is sensitive to blood flow in one direction at a time.

15. A venography system to discriminate venous blood flow from arterial blood flow and display an MR image with only a representation of one of arterial blood flow and venous blood flow comprising:

an MRI apparatus capable of producing arterial and venous signals from a monitored patient;

a user interface to select an MR image from a group consisting of an arterial only blood flow image and a venous only blood flow image;

a velocity encoding module connected to, and receiving the arterial and venous signals from, the MRI apparatus, and producing a VENC value that establishes a noise level in the phase image whose value is between that of the arterial signal and that of the venous signal in the phase image during a cardiac diastolic period of an MR image;

an image reconstruction module connected to the velocity encoding module to produce a magnitude image and a phase image; and a mask module connected to receive the magnitude and phase images and produce either one of the venous blood flow image and the arterial blood flow image based on an input to the user interface.

16. The venography system of claim 15 wherein the mask module comprises a subtraction submodule which receives and subtracts the venous only blood flow image from the magnitude image to create the arterial only blood flow image.

17. The venography system of claim 15 wherein the MRI apparatus provides a phase contrast sequence image during cardiac diastole.

18. The venography system of claim 15 wherein the image reconstruction module comprises:

a magnitude image reconstruction submodule connected to the velocity encoding module to produce the magnitude image; and a phase image reconstruction submodule connected to the velocity encoding module to produce the phase image.

19. The venography system of claim 15 further comprising:

an image selection module connected to the mask module and the user interface to select a desired image and provide a desired output; and a display to receive the desired output and display the desired image.

20. An MR venography apparatus for displaying only one of venous blood flow and arterial blood flow comprising:

means for acquiring an MRI;

means for ECG-gating MRI acquisitions during a diastolic period of a cardiac cycle;

means for encoding a velocity encoding value for suppressing arterial blood flow signals during the diastolic period MRI acquisitions;

means for reconstructing a magnitude image and a phase map image;

means for processing the reconstructed magnitude and phase map images to create venous only and arterial only output signals; and means for displaying one of the venous only output signal as a venous blood flow image and the arterial only output signal as an arterial blood flow image.

21. The MR venography apparatus of claim 20 further comprising:
   an output means for selecting which of the venous blood flow and arterial blood flow images to display.

22. The MR venography apparatus of claim 20 wherein the means for processing comprises:
   a means for masking the magnitude image with the phase map image; and
   a means for subtracting a result from the means for masking from the magnitude image.

23. The MR venography apparatus of claim 22 further comprising a selection control means for directing which of the venous and arterial blood flow images is displayed by the means for displaying.

24. The MR venography apparatus of claim 20 wherein the means for acquiring an MRI comprises means for acquiring an MRI with phase contrast sequence during diastole of the cardiac cycle.

* * * * *